(12) United States Patent
Bombardelli et al.

(10) Patent No.: US 9,248,157 B2
(45) Date of Patent: Feb. 2, 2016

(54) EXTRACTS OF CYNARA SCOLYMUS, COFFEA SSP. AND OLEA EUROPAEA FOR THE TREATMENT OF METABOLIC SYNDROME

(71) Applicant: INDENA S.P.A., Milan (IT)

(72) Inventors: Ezio Bombardelli, Gropello Cairoli (IT); Fabrizio Corti, Milan (IT)

(73) Assignee: INDENA S.P.A., Milan (IT)

( * ) Notice: Subject to any disclaimer, the term of this patent is extended or adjusted under 35 U.S.C. 154(b) by 0 days.

(21) Appl. No.: 14/426,504

(22) PCT Filed: Sep. 19, 2013

(86) PCT No.: PCT/EP2013/069455
§ 371 (c)(1),
(2) Date: Mar. 6, 2015

(87) PCT Pub. No.: WO2014/044744
PCT Pub. Date: Mar. 27, 2014

(65) Prior Publication Data
US 2015/0231193 A1    Aug. 20, 2015

(30) Foreign Application Priority Data

Sep. 20, 2012  (IT) .......................... MI2012A001570

(51) Int. Cl.

| | | |
|---|---|---|
| *A61K 36/00* | (2006.01) | |
| *A61K 36/63* | (2006.01) | |
| *A61K 36/74* | (2006.01) | |
| *A61K 36/28* | (2006.01) | |
| *A61K 31/216* | (2006.01) | |
| *A61K 31/353* | (2006.01) | |
| *A61K 31/365* | (2006.01) | |
| *A61K 36/53* | (2006.01) | |
| *A61K 31/7016* | (2006.01) | |
| *A61K 31/05* | (2006.01) | |

(52) U.S. Cl.
CPC ................. *A61K 36/74* (2013.01); *A61K 31/05* (2013.01); *A61K 31/216* (2013.01); *A61K 31/353* (2013.01); *A61K 31/365* (2013.01); *A61K 31/7016* (2013.01); *A61K 36/28* (2013.01); *A61K 36/53* (2013.01)

(58) Field of Classification Search
None
See application file for complete search history.

(56) References Cited

FOREIGN PATENT DOCUMENTS

EP    1967199    9/2008

OTHER PUBLICATIONS

"Vlle Symposium international d'aromatherapie et plantes medicinales, Grasse 2006 (II)", Phytotherapie; De la Recherche a La Pratique, Springer-Verlag, PA, vol. 5, No. 1, Apr. 26, 2007, pp. 41-47.
Pascual Fuster V et al., "New Concepts in Dietary Treatment of Metabolic Syndrome", Revista Clinica Espanola, Madrid, ES, vol. 206, No. 2, Feb. 1, 2006, pp. 100-102.
International Search Report and Written Opinion of the International Searching Authority for PCT/EP2013/069455, issued on Oct. 30, 2013.

*Primary Examiner* — Qiuwen Mi
(74) *Attorney, Agent, or Firm* — Silvia Salvadori, P.C.; Silvia Salvadori

(57) ABSTRACT

Disclosed is a composition comprising: a. *Cynara* extract having a caffeoylquinic acid content ranging from 30 to 45% by weight, a flavonoid content ranging from 8 to 16% by weight and a cynaropicrin content ranging from 10 to 18% by weight; b. *Coffea* spp. extract containing between 40% and 80% by weight of caffeoylquinic acids; c. *Olea europaea* extract containing between 30% and 40% polyphenols, with a verbascoside content exceeding 5% and a hydroxytyrosol content exceeding 1.5%.

12 Claims, No Drawings

EXTRACTS OF CYNARA SCOLYMUS, COFFEA SSP. AND OLEA EUROPAEA FOR THE TREATMENT OF METABOLIC SYNDROME

This application is a U.S. national stage of PCT/EP2013/069455 filed on 19 Sep. 2013, which claims priority to and the benefit of Italian Application No. MI2012A001570 filed on 20 Sep. 2012, the contents of which are incorporated herein by reference in their entireties.

SUMMARY OF THE INVENTION

The present invention relates to a novel combination of *Cynara scolymus*, *Olea europaea* and *Coffea* spp. extracts, which is useful for the prevention and treatment of dyslipidaemia, hyperglycaemia, inflammation and hypertension, which said parameters are characteristic of both metabolic syndrome and type 2 diabetes. The normalisation of said parameters also influences the increase in body weight that accompanies said syndromes through indirect mechanisms of hormonal modifications associated with the biochemistry of interaction with the enzymatic systems, thus reducing the cardiovascular risk.

As regards the lipid aspect, the combination of these extracts has proved to significantly increase the HDL cholesterol value in patients with below-average parametric values, favourably shifting the LDL/HDL ratio, especially in patients at risk of heart attack with dyslipidaemia of different etiologies.

An interaction by the polyphenols in the *Olea europaea* extract with the biochemical mechanisms of the adipose tissue that promote the release of pro-inflammatory cytokines has also been demonstrated. Said molecules are considered to be initiators of the processes that, by altering the vascular endothelium, promote the formation of atherosclerotic plaque. Said activities are additional to the ability to reduce the oxidative processes affecting the cLDL levels.

PRIOR ART

As known from the literature, extracts of artichoke (*Cynara scolymus*) are known for their choleretic, cholagogue, blood glucose-lowering, antidyspeptic and mildly cholesterol-lowering action; the cholesterol reduction reported in numerous clinical trials is modest, and never exceeds 10%, with variations between studies due to the quality of the protocols and the composition of the extracts used. According to the literature, the classes of active ingredients are caffeoylquinic acids, which perform a choleretic, blood glucose-lowering and liver-protecting effect; flavonoids, which perform a lipid-lowering effect associated with cholesterol synthesis; and cynaropicrin, which performs an anti-inflammatory action due to the interaction with nuclear factor NFkB and TNF-α.

Olive oil has always been considered a basic ingredient of the Mediterranean diet, which is still known to be the most natural form of prevention of metabolic syndrome. Continual progress in scientific studies has demonstrated that a range of micronutrients belonging to the chemical class of polyphenols, which are present in extra-virgin oil, even more than the composition in fatty acids, operates synergically through antioxidant activity and modulation of numerous enzymatic activities to defend the endothelium of the arterial vessels. Metabolic syndrome, which in Western countries is due to incorrect nutrition and a sedentary lifestyle, often leads to dyslipidaemia and obesity, with evident adverse consequences on the cardiocirculatory apparatus. The growing adipose tissue is infiltrated by macrophages, leukocyte cells that release pro-inflammatory cytokines and inflammation mediators such as COX-2 and iNOS; in addition, the circulating fatty acids act as messengers of the adipose cells through the TLR-4 receptors, which induce the expression of inflammatory mediators by activating NF-kB or JNK. This cascade of events generates a state called "silent inflammation", whose aggressive action against the vascular endothelia causes lesions that act as the site of attack by atheromatous plaque, which is mainly responsible for the atherosclerotic and thrombotic symptoms that form the basis of cardiovascular disease.

By the early 1990s, the chemical class of polyphenols, secondary metabolites of plants, had already been identified for its antioxidant capacity, and it had been observed that a diet rich in these compounds was correlated with a low incidence of cardiovascular disease and tissue aging. In particular two polyphenols present in the water-soluble part of the fruit of *Olea europaea*, verbascoside and hydroxytyrosol, have not only proved effective in tests in vitro, but have also given encouraging results in clinical trials. Hydroxytyrosol has received a favourable opinion from the EFSA for the indication as an inhibitor of LDL oxidation, one of the secondary phenomena that induce the formation of atheromatous plaque. Said two polyphenols are present in different quantities and ratios in the various olive cultivars, making them more or less suitable for the production of an enriched extract.

The process required to obtain extracts of *Cynara scolymus* and *Olea europaea*, which have long been known in both traditional and allopathic medicine, presents major problems of reproducibility and active ingredient content, with the result that the clinical data are erratic and of low therapeutic usefulness when compared with the current medicaments.

Extracts of *Coffea* spp., preferably *Coffea arabica*, prepared from the unroasted beans, present similar problems to those reported for *Cynara scolymus*, as there are no standard processes that provide pharmaceutical reproducibility. The low reproducibility of the extracts depends on several factors, such as the choice of plant biomass and its drying conditions. The production of the biomass constitutes a crucial stage of the process because the drying conditions, which are crucial to maintain the active ingredient content, depend on the growing period of the plant.

A huge amount of pharmacological and clinical literature claims many health-giving activities for artichokes, olives and coffee, but without adequately describing the extracts used; in fact, artichokes present composition problems associated with the degradation of some families of active ingredients.

The composition of olive extract is influenced by the use of the cultivar and different oil by-products, while the presence or absence of caffeine in coffee extracts involves problems associated with the often contradictory activities of said compound.

DESCRIPTION OF THE INVENTION

The present invention relates to compositions containing:
a. *Cynara* extract having a caffeoylquinic acid content ranging from 30 to 45% by weight, a flavonoid content ranging from 8 to 16% by weight and a cynaropicrin content ranging from 10 to 18% by weight;
b. *Coffea* spp. extract containing between 40% and 80% by weight of caffeoylquinic acids;
c. *Olea europaea* extract containing between 30% and 40% polyphenols, with a verbascoside content exceeding 5% and a hydroxytyrosol content exceeding 1.5%.

The *Cynara* sp. extract preferably has a caffeoylquinic acid content of 35±2%, a flavonoid content of 12±2%, and a cynaropicrin content of 13±2%.

The *Coffea* sp. extract preferably has a caffeoylquinic acid content of 60±2% by weight.

The weight ratio between *Coffea* sp. extract and *Cynara* sp. extract ranges between 0.5 and 2, and is preferably 1. The quantities of *Cynara* extract, *Coffea arabica* extract and *Olea europaea* extract range from 100 to 300 mg.

Selected artichoke cultivars, preferably *Cynara scolymus* or *Cynara cardunculus*, more preferably *Cynara scolymus*, are used to prepare the extract according to the invention. The methods of preparing the extract are reported in WO 2007/006391 and WO 2008/107183.

*Olea europea* extract, which is rich in verbascoside and hydroxytyrosol, can be prepared from olive pulp (U.S. Pat. No. 6,358,542), after extraction of the oily matrix by a preparation process that involves water-alcohol extraction, a stage on resin with water-alcohol elution, and a final drying stage. The finished product presents a final polyphenol concentration exceeding 30%, with a verbascoside content exceeding 5% and a hydroxytyrosol content exceeding 1.5%. The use of the Coratina cultivar is preferred. The end product, which has the tradename Oleaselect®, has demonstrated excellent activity, both in vitro and on volunteers, keeping the tissue damage parameters under control, especially during meals rich in fats, which are a major risk factor [Cerletti C. et al, SINUT Congress 2010, Milan].

The coffee extract is produced by water-alcohol extraction of the crushed beans, with aliphatic alcohols, preferably with ethanol, and after elimination of the caffeine by counter-extraction with ethyl acetate according to the procedure described in the examples, concentrated in a vacuum until dry.

*Coffea arabica* beans are extracted with aqueous ethanol until exhausted of polyphenols, and the partial extracts are combined and concentrated in a vacuum to water; after filtration of the insoluble materials the aqueous solution is basified with sodium bicarbonate and counter-extracted with a 9:1 mixture of ethyl acetate/hexane to eliminate the caffeine. After acidification to pH 2 the aqueous solution is absorbed on a polystyrene absorption resin wherein it is eluted with ethanol. The final extract is collected and concentrated in a vacuum until dry. An extract containing between 40 and 80% of caffeoylquinic acids, normally 60%, is obtained. As an alternative to the use of ethanol as solvent for elution of caffeoylquinic acids from resins, a 1 mM solution of KOH in water in the presence of nitrogen can advantageously be used until complete recovery of the caffeoylquinic acids; the weakly basic eluate is neutralised with cationic resin to pH 5, and concentrated until dry in a vacuum.

Alternatively, instead of being isolated with absorption resin, the caffeoylquinic acids can be isolated by counter-extraction at an acid pH with microfiltration through organic membranes and concentration by nanofiltration through a ceramic membrane to the desired concentration, and then dried in an atomiser.

The combined extracts have demonstrated considerable activity on the reduction of total cholesterol, LDL cholesterol and blood glucose. Increased cHDL, modulation of inflammatory parameters and reduced cardiovascular risk factors have also unexpectedly been observed.

According to a preferred aspect of the invention, one part of artichoke extract is mixed with one part of coffee extract to obtain, in the final extract, all the isomeric forms of chlorogenic acid, which is the main compound of the polyphenol family and dicaffeoyl derivatives. Flavonoids derived from luteolin and cynaropicrin, which perform a marked lipid-lowering action, also acting on the enzymes in the liver by regulating the biosynthesis of HDL, boost the global activity of the novel combination. The addition to these compounds of *Olea Europea* extract, preferably the extract called Oleaselect®, completes the activity of this mixture by providing complete protection against the degenerative effects of metabolic syndrome.

The combination according to the invention has demonstrated considerable activity in reducing total cholesterol, LDL cholesterol and blood glucose levels and increasing the cHDL levels, which was not foreseeable on the basis of the literature. In particular this combination significantly reduces the postprandial blood glucose level, clinically contributing to a marked reduction in body weight by reducing the fatty mass.

The combination according to the invention reduces cardiovascular risk, especially in diabetics, for the following reasons:

a) Improvement in blood lipid level
b) Reduction in blood glucose level
c) Reduction in body mass index (BMI).

The increase in cHDL is of great therapeutic importance because it is active on both primary dyslipidaemia and that induced by concomitant treatment with cholesterol-lowering medicaments, which naturally reduce the cHDL level as well as the cholesterol level. The advantage of this combination lies in the fact that the substances active on the above-mentioned parameters are potent bioavailable antioxidants which are consequently able to eliminate free radicals at both intestinal and vascular level after absorption. The antioxidant function that prevents oxidation of the cLDL cholesterol fraction, the phenomenon that precedes its deposit on the vessel wall, also develops in the liver with the advantage of liver detoxification and reduction of the liver steatosis observed in overweight individuals and, for different reasons, in diabetics.

It has surprisingly been found at clinical level that the combination unpredictably possesses a greater activity than that of the individual components taken at the same dose of active ingredients, especially as regards increasing HDL cholesterol and reducing the body mass index (BMI).

In particular, it should be emphasised (and this is the key point of the invention) that the unexpectedly high increase in HDL cholesterol is observed both in patients with hyperlipidaemia and in those with below-normal HDL cholesterol following treatment with statins or cholesterol-lowering medicaments. It also possesses an effective targeted anti-inflammatory action in obese and dyslipidaemic patients.

Modest, erratic increases in HDL cholesterol following the administration of several grams per day of *Cynara scolymus* extracts have been reported in the literature, but without any evidence of reproducibility or consistency. Moreover, artichoke extract has never been combined with coffee extract, although the latter is the plant richest in caffeoylquinic acids. For the artichoke, contradictory data of low practical significance have been reported for both HDL cholesterol and the reduction in total cholesterol (Naturmed, 13, 17-24, 1998, Arzneim-Forschung, 50, 260-65, 2000. The Cochrane Library, 2002, Issue 3).

Strengthening of both postprandial and fasting hypoglycaemic activity makes the combination according to the invention particularly suitable for nutraceutical use to reduce body weight, as it significantly reduces the body mass index.

Experimentation with the compositions according to the invention indicates a reduction of about 25% in total cholesterol and LDL cholesterol, and a significant 20% increase in HDL cholesterol. This increase, which was found to be constant over time on a case study of patients with total cholesterol ranging from 230 to 280 mg/dl, has never been described with previously known herbal preparations.

The formulations according to the invention have also proved effective on different parameters in a range of patients suffering from metabolic syndrome, in whom normalisation of parameters such as blood glucose, lipid parameters, hypertension and "silent inflammation" was observed.

According to a preferred aspect, the compositions according to the invention will be formulated as normal or gastroprotected capsules or tablets, to promote topical local activity while leaving the digestive function unchanged at stomach level.

Said compounds will preferably be administered to humans in oils rich in ω-3 fatty acids to facilitate absorption of the cynaropicrin present in *Cynara scolymus* extract and of the caffeoylquinic acids and polyphenols in Oleaselect®.

According to a further aspect, the compositions according to the invention may be administered together with other substances having a useful or complementary activity.

The compositions according to the invention will be formulated according to conventional methods, such as those described in "Remington's Pharmaceutical Handbook", Mack Publishing Co., N.Y., USA. In particular, the compositions according to the invention will be formulated according to conventional plant ingredient formulation techniques, which require particular care to be taken to avoid interactions with the excipients and the capsule matrices. Examples of oral formulations are tablets, dragées, soft and hard gelatin capsules, and cellulose capsules.

The examples set out below further illustrate the invention.

Example 1

Preparation of *Coffea arabica* Extract

10 Kg of *Coffea arabica* beans are finely ground and extracted with an 85% v/v mixture of ethanol and water containing a quantity of $H_2SO_4$ sufficient to maintain the pH at 2.5, until exhaustion of caffeoylquinic acids. The extraction is performed at the temperature of 50° C. The water-alcohol solution is concentrated to 10 L, and the water-insoluble products are then filtered. The aqueous solution is alkalinised to pH 7.6 and counter-extracted with a 9:1 mixture of ethyl acetate and hexane until the caffeine present has been almost totally eliminated. After elimination of the residual solvents in a vacuum, the solution is acidified to pH 4 and subjected to nanofiltration through an N30F membrane with a 400 D cut-off. The caffeoylquinic acids are concentrated in the retentate, while salts and sugars and undesirable products with a low molecular weight are removed from the permeate. The retentate is concentrated to a dry residue of 10% and atomised. 600 g of a pale beige extract is obtained, which has a caffeoylquinic acid content of 56%, measured by HPLC, and a chlorogenic acid content of 32%.

Example 2

Soft Gelatin Capsules

Unit Composition

| | |
|---|---|
| *Cynara scolymus* extract | 200 mg |
| *Coffea arabica* extract | 100 mg |
| *Olea europea* extract | 250 mg |
| Soya lecithin | 10 mg |
| Linseed oil | q.s. for 900 mg |

Reference Example 3

Tablets

Unit Composition

| | |
|---|---|
| *Cynara scolymus* extract | 200 mg |
| *Coffea arabica* extract | 150 mg |
| Oleaselect ® | 250 mg |
| Microcrystalline cellulose | 300 mg |
| Calcium phosphate dihydrate | 100 mg |
| Silicon dioxide | 12 mg |
| Magnesium stearate | 8 mg |

Example 4

Treatment of Patients Suffering from Metabolic Syndrome

A clinical trial was conducted on four groups of patients with metabolic syndrome who presented elevated total cholesterol, triglyceride, LDL cholesterol, and blood glucose values.

The four groups of patients were treated for three months with the composition according to the invention reported in example 2 (Group 4), and with the active components thereof in the same quantities as present in the composition: Group 1: *Coffea arabica* extract 100 mg; Group 2: *Cynara scolymus* extract 200 mg; Group 3: Oleaselect® 250 mg. The capsules were administered at the main meal. The mean initial values of total cholesterol, LDL cholesterol, HDL cholesterol, triglycerides, blood glucose and body mass index (BMI), and the percentage variations in those values after one month's treatment, are set out in the tables below.

TABLE 1

| Group | Mean value of total cholesterol before treatment | % variation in mean value of total cholesterol after 1 month's treatment | Mean value of LDL cholesterol before treatment | % variation in mean value of LDL cholesterol after 1 month's treatment | Mean value of HDL cholesterol before treatment | % variation in mean value of HDL cholesterol after 1 month's treatment |
|---|---|---|---|---|---|---|
| Group 1 (10 patients) | 267 | −2.6 | 172 | −3.4 | 35 | −5.1 |
| Group 2 (20 patients) | 278 | −4.1 | 188 | −5.2 | 34 | 6.5 |

TABLE 1-continued

| Group | Mean value of total cholesterol before treatment | % variation in mean value of total cholesterol after 1 month's treatment | Mean value of LDL cholesterol before treatment | % variation in mean value of LDL cholesterol after 1 month's treatment | Mean value of HDL cholesterol before treatment | % variation in mean value of HDL cholesterol after 1 month's treatment |
|---|---|---|---|---|---|---|
| Group 3 (19 patients) | 271 | −6.2 | 181 | −5.6 | 36 | 3.2 |
| Group 4 (23 patients) | 275 | −26 | 198 | −24.8 | 33 | 25 |

TABLE 2

| Group | Mean value of triglycerides before treatment | % variation in mean value of triglycerides after 1 month's treatment | Mean value of blood glucose before treatment | % variation in mean value of blood glucose after 1 month's treatment | Mean BMI value | % variation in mean BMI value after one month's treatment |
|---|---|---|---|---|---|---|
| Group 1 (10 patients) | 285 | −5.1 | 142 | −4.1 | 28 | −0.2 |
| Group 2 (20 patients) | 256 | −8.0 | 131 | −4.9 | 29 | −1.2 |
| Group 3 (20 patients) | 273 | −6.3 | 129 | −1.6 | 27 | −1.3 |
| Group 4 (23 patients) | 267 | −41 | 130 | −22.4 | 28 | −8.5 |

The invention claimed is:

1. A composition comprising:
   a. an extract of *Cynara* having a caffeoylquinic acid content ranging from 30 to 45% by weight, a flavonoid content ranging from 8 to 16% by weight and a cynaropicrin content ranging from 10 to 18% by weight;
   b. an extract of *Coffea* spp. having a caffeoylquinic acid content ranging from 40% to 80% by weight;
   c. an extract of *Olea europaea* having a polyphenol content ranging from 30% to 40% with a verbascoside concentration higher than 5% and a hydroxytyrosol concentration higher than 1.5%, wherein the amounts of the extract of *Cynara* extract, *Coffea* extract and *Olea europaea* extract range from 100 to 300 mg.

2. The composition according to claim 1 wherein the *Cynara* extract has a caffeoylquinic acid content of 35±2% by weight, a flavonoid content of 12±2% by weight and a cynaropicrin content of 13±2% by weight.

3. The composition according to claim 1 wherein the *Coffea* spp. extract has a caffeoylquinic acid content of 60±2% by weight.

4. The composition according to claim 1 wherein the *Olea europaea* extract has a polyphenol content of 30±2% with a verbascoside concentration higher than 5% and a hydroxytyrosol concentration higher than 1.5%.

5. The composition according to claim 1 wherein the extract of *Cynara* is the extract of *Cynara* scolymus or *Cynara cardunculus*.

6. The composition according to claim 1 wherein the *Coffea* spp. extract is the extract of *Coffea arabica*.

7. The composition according to claim 1 wherein the weight ratio of the *Cynara* extract to the *Coffea* spp. and *Olea europaea* extracts ranges from 0.5 to 2.

8. A method of treating patients suffering from metabolic syndrome with a composition according to claim 1 said method comprising:
   administering an effective amount of said composition to said patients, thereby treating said metabolic syndrome.

9. The method of treating patients suffering from type 2 diabetes with a composition according to claim 1, said method comprising:
   administering an effective amount of said composition to said patients, thereby treating said type 2 diabetes.

10. The method of treating patients suffering from hyperglycaemia, hypercholesterolaemia, hypertension and obesity with a composition according to claim 1 said method comprising:
    administering an effective amount of said composition to said patients, thereby treating said hyperglycaemia, hypercholesterolaemia, hypertension and obesity.

11. A pharmaceutical composition comprising as active ingredient a composition of claim 1 in admixture with at least one pharmaceutically acceptable excipient or carrier.

12. The pharmaceutical composition according to claim 11 wherein the carrier is an oil comprising Omega-3 unsaturated fatty acids.

* * * * *